United States Patent [19]

Shumakov et al.

[11] 4,162,543
[45] Jul. 31, 1979

[54] ARTIFICIAL HEART

[75] Inventors: Valery I. Shumakov; Moisei A. Lokshin; Vadim V. Vlasov; Vitaly A. Burynin; Nikolai V. Novikov, all of Moscow, U.S.S.R.

[73] Assignee: Institut Transplantatsii Organov I Tkanei, U.S.S.R.

[21] Appl. No.: 827,029

[22] Filed: Aug. 23, 1977

[51] Int. Cl.$^2$ .................. A61F 1/24; A61M 1/03
[52] U.S. Cl. .................................. 3/1.7; 128/1 D
[58] Field of Search .......... 3/1.7, 1; 128/1 D, DIG. 3

[56] References Cited

U.S. PATENT DOCUMENTS

| | | | |
|---|---|---|---|
| 3,491,377 | 1/1970 | Bolie | 3/1 |
| 3,783,453 | 1/1974 | Bolie | 3/1.7 |
| 3,966,358 | 6/1976 | Heimes et al. | 3/1.7 X |
| 3,974,825 | 8/1976 | Normann | 3/1.7 X |

OTHER PUBLICATIONS

"Servomechanism to Drive an Artificial Heart Inside the Chest", by K. W. Hiller et al., Transactions American Society for Artificial Internal Organs, vol. XIII, 1962, pp. 125–130.
"An Electronic-Mechanical Control for an Intrathoracic Heart", by K. W. Hiller et al., American Journal of Medical Electronics, Jul.–Sep. 1963, pp. 212–221.
"Development of an Artificial Intrathoracic Heart", by C. K. Kirby et al., Surgery, vol. 56, No. 4, Oct. 1964, pp. 719–725.

Primary Examiner—Ronald L. Frinks
Attorney, Agent, or Firm—Steinberg & Blake

[57] ABSTRACT

An artificial heart comprising at least one blood circulating pump having a transparent housing divided into two chambers by a diaphragm. One of the chambers is a hydraulic chamber having an inlet valve and an outlet valve which are connected to the circulatory system; the other chamber is a pneumatic chamber provided with a nipple for the intake and discharge of gas. The pump's pneumatic chamber has a transparent conductive coating, for example, of gold, applied onto the internal wall of said pneumatic chamber. Said coating and the surface of the blood circulating in the hydraulic chamber make up a capacitor whose capacity varies due to changes in the volume of the hydraulic chamber. Said capacitor serves as a blood volume transducer. The artificial heart includes a system for controlling the supply of gas to and the discharge of gas from the pneumatic chamber of said pump. The control system comprises an element which is sensitive to variations in the blood volume. Said sensitive element is an RC bridge. Said blood volume transducer is connected in one of the arms of said bridge. A blood volume indicator is connected to the output of the sensitive element.

9 Claims, 8 Drawing Figures

ARTIFICIAL HEART

BACKGROUND OF THE INVENTION

1. Field of the Invention

The present invention relates to medical equipment and, more particularly, to an artificial heart and is used to provide for autonomous and auxiliary circulation in experimental and clinical conditions.

Vital activity is marked by significant changes in the vascular tension and the amount of blood passed through the greater and lesser circulation pumps. Therefore, to control an artificial heart, one has to adjust its rhythm and maintain a constant stroke volume irrespective of variations in the peripheral vascular resistance or the resistance of the pneumatic piping. In doing so, special attention must be paid to the interaction between the right and left pumps of the artificial heart, and utmost care must be taken to avoid the pumping of blood from one circulation to the other, which otherwise may lead to irreversible deposition of blood either in the pulmonary or systemic circulation.

There is known an artificial heart of the type that comprises blood circulating pumps, each having a housing with a diaphragm installed in said housing and dividing it into two chambers, i.e. a hydraulic chamber and a pneumatic chamber. The hydraulic chamber has an inlet valve and an outlet valve incorporated in the blood circulation system. There are known pumps of the type that comprises an instantaneous blood volume transducer of the induction type (cf. US Patent Specification No. 3,491,377, Cl. 3-1, of 1970).

2. Description of Prior Art

Devices of the aforesaid type, comprising an induction transducer to monitor instantaneous blood volume values in the hydraulic chamber, have a number of disadvantages. An artificial heart of this type may fail to function properly due to the effects of external magnetic fields. A non-uniform deflection of the movable part of the pump affects the accuracy of the signal which is proportional to the instantaneous blood volume. The presence of metal components attached to the movable elastic part of the pump (a diaphragm or an elastic bag) tells on the service life of the pump.

Of course, the foregoing type of pump can incorporate a capacitive transducer for monitoring the volume of blood in the hydraulic chamber. It is clear, however, that the capacitive transducer is as disadvantageous as the induction transducer.

There are known artificial heart control systems of the type that comprises sensitive elements accomodated in the right and left pumps. Said elements are sensitive to the volume of blood in the respective pump. Each of said sensitive elements is coupled via a converter and a threshold unit to a unit for setting the duration of compressed gas intake. The latter unit switches an electropneumatic valve through which the gas chamber of a respective pump is alternately connected to compressed and rarefied gas units.

One such system comprises a servovalve controlled by an electronic device (cf. K. W. Hiller, W. Seidel and W. J. Kolff, "An Electronic Mechanical Control for an Intrathoracic Artificial Heart," An. J. Med. Electron., 1963).

This system is disadvantageous in that it calls for an operator to continuously check and balance the deliveries of both pumps in case of changes in the peripheral vascular resistance or serious loss of blood.

The difficulty of adjusting the pressure in the pneumatic chambers is partially overcome in another known device, wherein the stroke volume is adjusted with the aid of diaphragm limit position sensors (cf. M. J. Crossby, "On the Control of Artificial Hearts," Cardiac Engineering, vol. 3, pp. 88-114, 1970).

The latter device is disadvantageous in that it only controls the duration of the compressed gas intake. The complete duration of the diaphragm's motion, which corresponds to the stroke volume, remains uncontrolled, which may lead to an inadequate exchange of blood between the greater and lesser circulations and the pumping of blood to a greater or lesser circulation alone. In addition, the combination of the electrical and mechanical components gives rise to a number of problems which limit the service life of the artificial heart.

There is further known a device which is intended to provide an optimum solution to the problem of improving the selection of time intervals between the onset and end of the delivery and suction phases of each pump (cf. USSR Inventor's Certificate No 434,941, Cl. AG1 F 1/24, granted on an application filed in 1971). This device is disadvantageous in that it only controls the time during which pressure is applied, but not the complete blood delivery and suction time.

On of the basic disadvatages of all of the foregoing devices is the lack of means to maintain equal deliveries of both pumps irrespective of variations in the peripheral vascular resistance or the resistance of the pneumatic lines.

It is an object of the present invention to ensure an equal exchange of blood between the greater and lesser circulations irrespective of changes in the peripheral vascular resistance.

It is another object of the invention to ensure a constant stroke volume of pumps.

It is still another object of the invention to make it possible to balance the exchange of blood between the greater and lesser circulations.

It is yet another object of the invention to make an artificial heart sensitive to the venous return.

It is also an object of the invention to make an artificial heart sensitive to changes in the arterial pressure.

Finally, it is an object of the invention to provide a possibility of visually checking the discharge of air from the hydraulic chamber.

SUMMARY OF THE INVENTION

The foregoing objects are attained by providing an artificial heart comprising at least one blood circulating pump having a transparent housing divided into two chambers by a diaphragm. One of the two chambers is a hydraulic chamber having an inlet valve and an outlet valve which are connected to the circulation system. The second chamber is a pneumatic chamber having a nipple for the supply and discharge of gas. The pump's pneumatic chamber is provided with a conducting transparent coating, for example, of gold, applied onto the internal wall of said pneumatic chamber. Said coating and the surface of the blood circulating in the hydraulic chamber make up a capacitor whose capacity varies due to changes in the volume of the hydraulic chamber. Said capacitor serves as a transducer of the blood volume in the pump. The artificial heart also includes a system for controlling the supply of gas to and the discharge of gas from the pneumatic chamber of said pump, which control system comprises electric and pneumatic power sources. The control system also incorporates an element which is sensitive to variations in the blood volume in the pump's hydraulic chamber, which sensitive element is an RC bridge one of whose arms incorporates said blood volume transducer. A blood volume indicator is connected to the output of the sensitive element. The control system further includes a compressed gas unit and a rarefied gas unit, whose inlets are connected to the pneumatic power source; an electropneumatic valve having two pneumatic inputs connected to the compressed and rarefied gas units, respectively, as well as one electric input and one pneumatic output connected through a pneumatic line to said nipple of the pump's pneumatic chamber;

a clock pulse generator performing the function of a pulse setting unit; a unit for setting the duration of the compressed gas intake, connected with its input to the clock pulse generator, and with its output to the electric input of said electropneumatic valve.

The foregoing design of the pump, provided with an indicator of the blood volume in the pump's hydraulic chamber, makes it possible to directionally alter the parameters of the compressed and rarefied gas units and visually check the discharge of air from the pump's hydraulic chamber as it is being filled with blood.

It is expedient that the artificial heart control system should be provided with a standard signal unit whose voltage corresponds to the final systolic blood volume of the pump, and a comparator having two inputs and an output. One of the comparator's inputs is connected to the standard signal unit, while the second input is connected to the output of said sensitive element. The output of the comparator is connected to the electric input of the compressed gas unit.

This makes it possible to stabilize the final systolic blood volume and make the artificial heart sensitive to changes of the blood pressure at the pump's outlet.

The function of the clock pulse generator can be performed by a threshold device to register the initial blood volume of the pump. The threshold device is connected with its input to the output of the sensitive element which is sensitive to variations in the blood volume; the output of the threshold device is connected to said unit for setting the duration of the compressed gas intake.

This makes the artifical heart sensitive to the venous return and stabilizes the stroke of the pump.

Provision of automatic control of the duration of the supply of compressed gas to the pneumatic chamber of the pump considerably simplifies the artificial heart control system and reduces its size. For this purpose, the time setting circuit of the duration setting unit is connected via the second input of said duration setting unit to the output of the comparator, while the output of the comparator is disconnected from the electric input of the compressed gas unit. This simplifies the control system, makes the artificial heart sensitive to the venous return and ensures a stable stroke volume of the pump.

The two pumps of the artificial heart, i.e. the first and second pumps respectively connected to the greater and lesser circulations and having blood volume transducers connected to the elements of the control system, which are sensitive to variations in the blood volume in the respective hydraulic chambers, provide for an adequate exchange of blood between the greater and lesser circulations, depending on changes in the peripheral vascular resistance of the greater circulation. For this purpose, the control system incorporates a comparator connected with one of its inputs to the output of the sensitive element of the first pump, and with its second input to the output of the sensitive element of the second pump, the output of said comparator being connected to the electric input of the compressed gas unit of the second pump. The control system may include a unit for setting the duration of the compressed gas intake, connected with its output to the electric inputs of the electropneumatic valves.

It is advisable that the artificial heart control system should include comparators and threshold devices connected in the control circuit of each pump. The control system should also include a number of units which are common for both pumps, such as a logical OR element, a unit for setting the duration of the compressed gas intake, and a standard signal unit with the voltage at the output of the latter corresponding to the final systolic blood volume of the pump. One input of each comparator is to be connected to the output of the respective sensitive element; the other input of each comparator is to be connected to the standard signal unit. The inputs of the threshold devices are to be connected to the respective outputs of the sensitive elements. The outputs of the threshold devices are to be connected to the respective inputs of the logical OR element whose output is to be connected to the input of the duration setting unit.

This equalizes the exchange of blood between the greater and lesser circulations irrespective of changes in the peripheral vascular resistance, stabilizes the stroke volume of the pump which is the first to be filled and improves the sensitivity of the artificial heart to the venous return.

The control system should include two units for setting the duration of the compressed gas intake, one for each pump. The time setting circuits are to be connected via the second inputs of the duration settling units to the outputs of the respective comparators, which outputs must be disconnected from the electric inputs of the respective compressed gas units.

This substantially simplifies the control circuit and reduces its dimensions.

Other objects and advantages of the present invention will be more readily understood from the following detailed description of a preferred embodiment thereof to be read in conjunction with the accompanying drawings, wherein.

DESCRIPTION OF A PREFERRED EMBODIMENT

Figure 1:
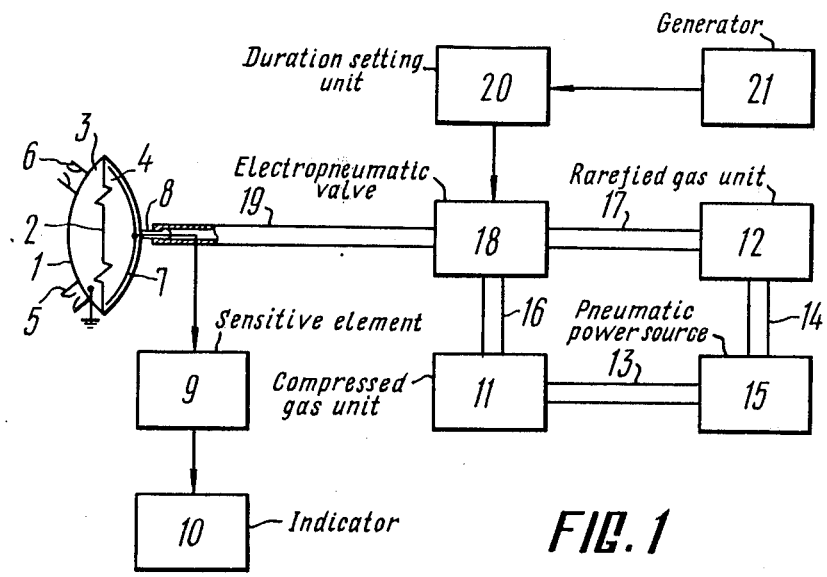
FIG. 1 is a general block diagram of an artificial heart comprising one pump with a blood volume transducer and a control system with a stroke volume indicator, in accordance with the invention.

FIG. 1 is a block diagram of an artificial heart comprising at least one blood circulating pump 1 with an indicator. The pump 1 has a transparent housing divided into two chambers by a diaphragm 2. The two chambers are a hydraulic chamber 3 and a pneumatic chamber 4. The hydraulic chamber 3 has an inlet valve 5 connected to the venous bed, and an outlet valve 6 connected to the arterial bed of the circulation system.

An almost transparent layer 7 of a conductive material, for example, gold, is applied onto the internal surface of the stationary part of the pneumatic chamber 4. Said layer 7 and the surface of the blood in the chamber 3 make up a capacitor transducer whose electric capacity varies depending on changes in the volume of the chamber 3. An almost transparent layer of gold, which serves as a screen (not shown), is applied onto the external surface of the stationary part of the chamber 4. The layer 7 has a contact which extends through the nipple 8 for the supply and discharge of gas and is connected by means of a shielded wire (not shown in FIG. 1) to an element 9 sensitive to variations in the volume of blood in the hydraulic chamber 3. The output of the sensitive element 9 is connected to an indicator 10 which is a neon discharge indicating lamp graduated in cm$^3$. The luminescence spectrum of the neon column of the indicator 10 is dependent on the input signal, which means it is proportional to the magnitude of the control current and, consequently, to the volume of blood forced from the hydraulic chamber 3.

The chamber 3 is alternately filled and emptied with the aid of a compressed gas unit 11 and a rarefied gas unit 12 which are connected by means of respective lines 13 and 14 to a pneumatic power source 15. The outlets of the units 11 and 12 are connected through lines 16 and 17 to the pneumatic inputs of an electopneumatic valve 18 whose output is connected by a line 19 to the nipple 8 of the pneumatic chamber 4. The electric input of the valve 18 is connected to the output of a unit 20 for setting the duration of the compressed gas intake, whose input is connected to a clock pulse generator 21 which performs the function of a pulse setting unit.

The generator 21 is either a multivibrator or a blocking generator. Likewise, the unit 20 for setting the duration of the compressed gas intake is a multivibrator.

Variable resistors of the time setting circuits of the generator 21 and the unit 20 are used to adjust the pulse rate and the duration of the compressed gas intake.

The electropneumatic valve 18 is a conventional three-way solenoid valve which may have one steady state, provided with a return spring.

The function of the compressed gas unit 11 and the rarefied gas unit 12 can be performed, for example, by stabilizing reducers, wherein the outlet pressure is adjusted by hand, by changing the position of the flapper. The function of said units 11 and 12 can also be performed by such commonly used actuators as electropneumatic transducers; the pressure of compressed or rarefied gas at the outlet of such a transducer is dependent on the magnitude of control current which controls the flapper position.

The pneumatic power source 15 comprises a conventional compressor and a vacuum pump; in some cases only a compressor is used.

As pointed out above, the element 9, which is sensitive to variations in the volume of blood in the hydraulic chamber 3 of the pump 1, senses changes in the volume of the chamber 3 from changes in the electric capacity between the stationary semitransparent layer 7 and the surface of the blood which comes into contact with the elastic diaphragm 2 in the chamber 3 as the latter is alternately filled with blood and emptied.

All the electronic components of the artificial heart are powered by an electric power source (not shown).

Figure 2:
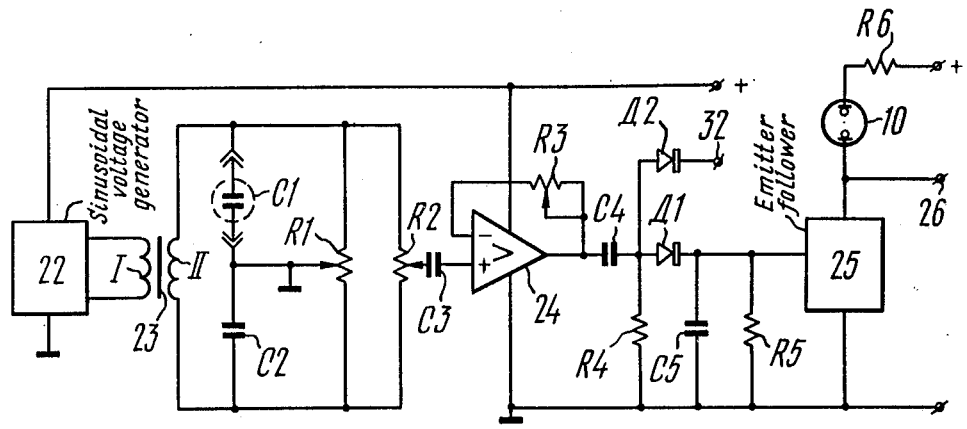
FIG. 2 is a key and functional diagram of an element sensitive to changes in the volume of blood in the hydraulic chamber of the pump, in accordance with the invention.

FIG. 2 is a diagram of the sensitive element 9.

A conventional sinusoidal voltage generator 22 is connected with its output via an isolation transformer 23 to the diagonal of an RC bridge. The blood volume transducer (a capacitor C1) is incorporated in one of the arms of said RC bridge.

The stationary part of the pneumatic chamber 4 (FIG. 1) with the semitransparent layer 7 is connected to one of the terminals of the secondary winding of the transformer 23. An electric potential is transmitted from the surface of the blood in the hydraulic chamber 3 through the circulation, picked up from a "grounded" part of the patient's body, for example, from the right leg, and applied to the common bus of the control system of the artificial heart (not shown). A calibration capacitor C2 is electrically interposed between the common bus and the other terminal of the secondary winding of the transformer 23. Potentiometers R1 and R2 are connected to the same secondary winding. The potentiometer R2 serves to zero the RC bridge when the pump is filled with blood. As blood is forced from the chamber 3, an error signal is picked off the slide of said potentiometer R2. The greater the volume of blood discharged from the chamber 3, the greater the amplitude of the error signal. The potentiometer R1 serves to improve the linearity of the voltage characteristic at the output of the RC bridge, depending on the volume of discharged blood.

One end of the measuring diagonal of the RC bridge is connected to the common bus; the other end of said measuring diagonal is coupled via a duct capacitor C3 to one of the inputs of a conventional operational amplifier 24 whose gain factor is controlled by a variable resistor R3. The output of the operational amplifier 24 is connected via an isolation circuit C4, R4 to a detector D1 with a filter C5, R5 connected to the input of an emitter follower 25 which controls the current of the indicator 10 interposed between the collector of the emitter follower 25 and the power source.

The emitter follower 25 has an additional output 26 for hooking recording equipment (not shown).

Figure 3:
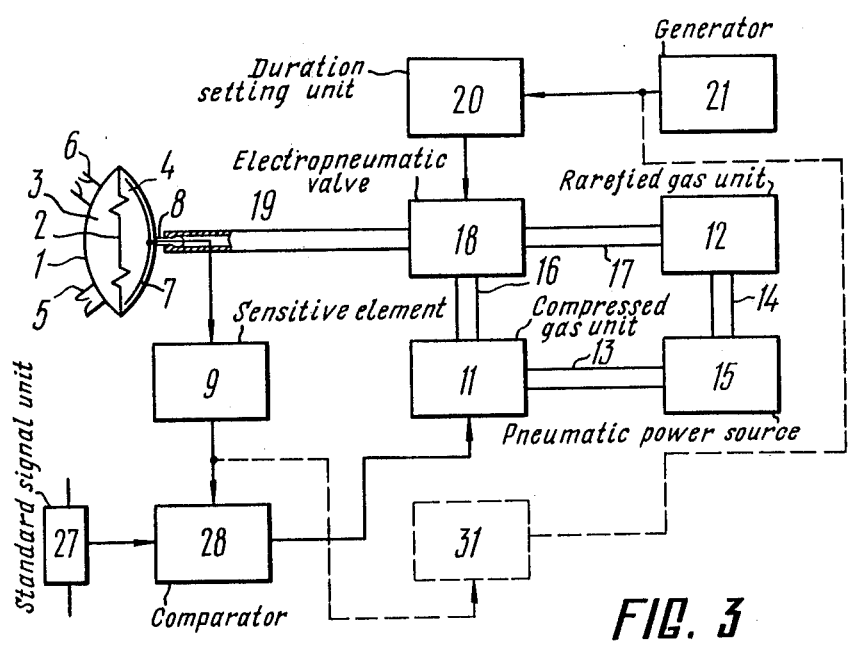
FIG. 3 is a block diagram of an artificial heart with one pump and a control system which stabilizes the stroke volume by changing the compressed gas pressure, in accordance with the invention.

FIG. 3 is a block diagram of an artificial heart sensitive to variations in the arterial pressure. For this purpose, the aforesaid system for controlling the supply of gas to and the removal of gas from said pneumatic chamber 4 of said pump 1 is provided with a transducer 27 of a standard signal of stroke blood volume, and a comparator 28. The latter has two inputs and one output. One of the inputs is connected to the sensitive element 9, whereas the second input is connected to the transducer 27 of a standard signal of the pump's stroke volume. The output of the comparator 28 is connected to the electric input of the compressed gas unit 11.

As is often the case with similar devices, the comparator 28 is a differential or balancing circuit. A d.c. voltage signal is applied to one of the inputs of said circuit from the output of the sensitive element 9; d.c. reference voltage is applied to the other input of said circuit, which reference voltage is compared to a signal of the blood volume transducer, i.e. a signal arriving from the standard signal transducer 27.

The transducer 27 is conventional small-resistance potentiometer connected to a d.c. source. Reference voltage picked off the slide of the potentiometer corresponds to a desired stroke volume of blood discharged from the chamber 3.

As pointed out above, the compressed gas unit 11 is a conventional electropneumatic converter; the compressed gas pressure at it outlet depends on the magnitude of current which controls the position of the flapper.

The remaining components of the artificial heart of FIG. 3 are interconnected as described above.

An artificial heart can be made sensitive to changes in the arterial pressure at the pump's outlet by changing the period of time during which compressed gas is directed to the chamber 4; the compressed gas pressure is maintained at a constant level.

Figure 4:
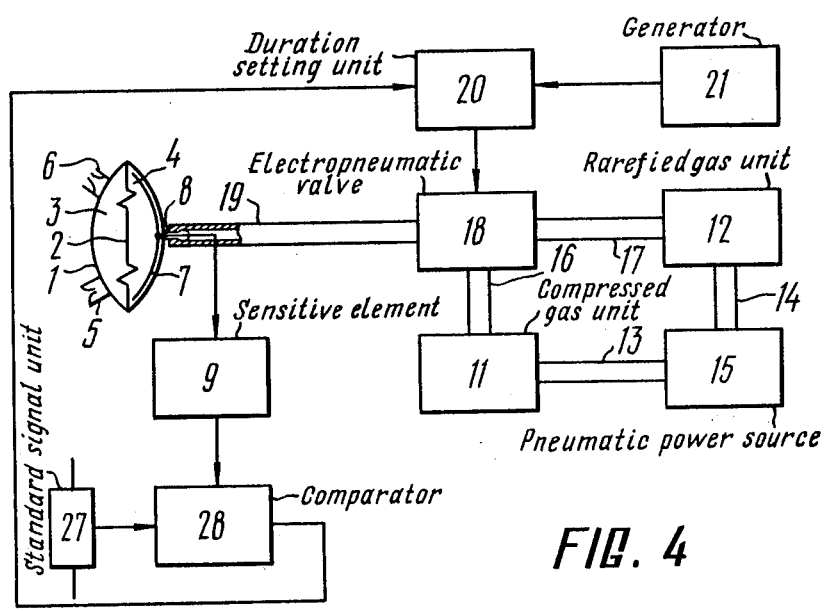
FIG. 4 is a block diagram of an artificial heart with one pump and a control system which stabilizes the stroke volume by changing the duration of the compressed gas intake, in accordance with the invention.

FIG. 4 is a block diagram of a system for automatically adjusting the duration of the supply of compressed gas to the pneumatic chamber, depending on changes in the arterial pressure. The compressed gas pressure in the unit 11 is set at a constant level and is somewhat higher than the pressure to be maintained at a normal arterial pressure and pulse rate, provided that these parameters do not vary within broad limits.

In the latter artificial heart control system, the output of the comparator 28 is connected to the second input of the unit 20 for setting the duration of the compressed gas supply.

Figure 5:
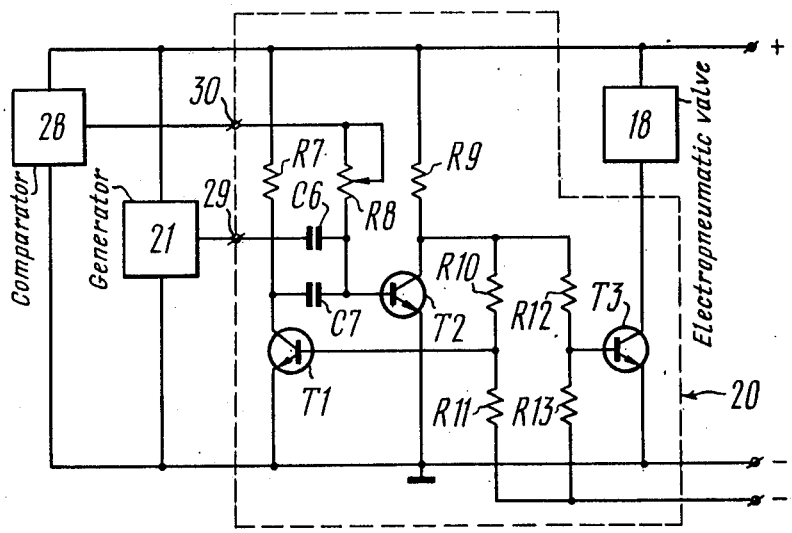
FIG. 5 is a key and functional diagram of the unit for setting the duration of the compresses gas intake, in accordance with the invention.

FIG. 5 is a key diagram of the unit 20 and shows its connections with other components of the artificial heart. The unit 20 is a monostable multivibrator, connected to the output of the generator 21. The generator 21 applies negative pulses via a first input 29 and a capacitor C6 to said multivibrator and thus actuates it. The comparator 28 adjusts the duration of output signals of the multivibrator. The comparator 28 is connected with its output to a second input 30 of the unit 20. A change of voltage across the input 30 changes the charging current of a capacitor C7 of a time setting circuit R7, C7 of the multivibrator.

The output of the multivibrator (the collector of a transistor T2) is coupled via an inverting amplifier, built around a transistor T3, to the electric input of the electropneumatic valve 18. A time setting circuit R8, C7 forms a signal which determines the period of time during which the pneumatic chamber 4 of the pump is connected to the compressed gas unit 11 (FIG. 4). The recharging time of the capacitor C7 depends on the voltage across the output of the comparator 28 which is inversely proportional to the value of the arterial blood pressure at the pump's outlet.

The sensitivity of the artificial heart to the venous return can be improved by varying the pump's diastole period, while keeping the stroke volume at a constant level (see FIG. 3). For this purpose, the generator 21 is disconnected from the output of the comparator 28 and replaced by a threshold device 31 whose input is connected to an output 32 of the sensitive element 9 (FIG. 2), whereas the output of the threshold device 32 is connected to the input of the unit 20 as shown by the dash line in FIG. 3.

The function of the threshold device can be performed by a Schmitt trigger having a capacitor connected to its input. Said capacitor and the trigger's input impedance serve as a filter whose time constant is equal to 2 to 3 frequency periods of the reference generator 22 (FIG. 2) which feeds power to the bridge incorporating C1, C2 and R1, R2.

In the course of operation of an intrapericardially implanted artificial heart, which fully replaces the natural heart with its two halves functioning as pumps, there are but small variations in the arterial pressure in the lesser circulation. Hence, there are small changes in the stroke volume of the pump connected in the lesser circulation.

Meanwhile, the blood pressure changes within broad limits in the greater circulation; hence, there are corresponding changes in the stroke volume of the pump placed in the greater circulation.

In order to avoid the pumping of blood from one circulation to the other, it is necessary to maintain equal deliveries of both pumps.

Figure 6:
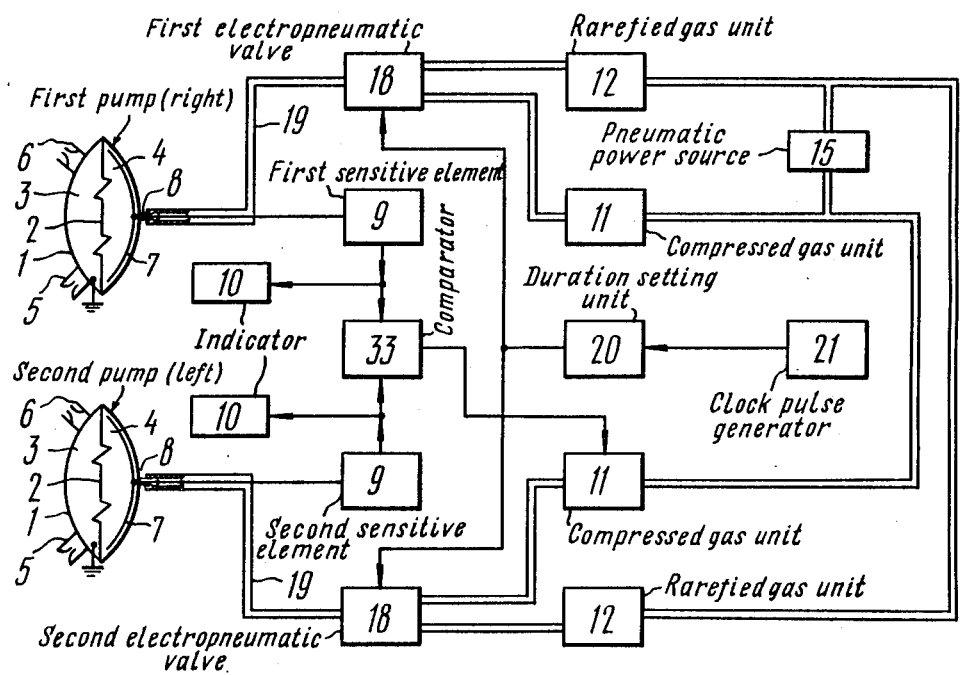
FIG. 6 is a block diagram of an artificial heart with two pumps and a control system which equalizes the stroke volumes of the two pumps, in accordance with the invention.

FIG. 6 is a block diagram of an artificial heart provided with a comparator to compare the stroke volumes of the pumps. The artificial heart comprises two blood circulating pumps, left and right, which are similar to the one described above.

The output of each sensitive element 9 of the respective pump is connected to the indicator 10 (FIG. 2) and to a common comparator 33 intended to compare the stroke volumes of both pumps. The comparator 33 is incorporated in the system for controlling the supply and discharge of gas and has two inputs, one for each pump, and an output connected to the electric input of the compressed gas unit 11 of the second (left) pump.

The stroke volume reference signal is a signal at the output of the sensitive element 9 of the right pump, which is connected to one of the inputs of the comparator 33. The other input of said comparator 33 is connected to the output of the sensitive element 9 of the second pump. The difference between the values of these signals, picked off the output of the comparator 33 as voltage, serves to adjust the compressed gas pressure at the outlet of the compressed gas unit 11 whose electric input is connected to the output of the comparator 33; it also serves to adjust the stroke volume of the left pump, keeping it equal to that of the right pump.

The duration unit 20 and the generator 21 are common for both pumps. The output of the unit 20 is connected to the electric inputs of both electropneumatic valves 18. The connections between the remaining artificial heart components (FIG. 6) are similar to those described above for the case of one pump (FIG. 3).

Operation of an artificial heart may be accompanied by a leakage of blood from one of the circulations or a deposition of blood in the organs of one of the circulations. In such a case it is necessary to add some blood to the organism to maintain normal pressure at the inlets of the artificial heart's pumps. After a return of the blood deposited by the organism or an addition of blood to one of the circulations, it is necessary to restore the normal blood pressure at the inlets of the pumps so as to equalize the minute volumes of both pumps. It should also be pointed out that the introduction of medicinal preparations may lead to substantial changes in the peripheral vascular resistance of one of the circulations, which entails a change in the stroke volume of one of the pumps and brings about an unequal exchange of blood between the greater and lesser circulations.

Figure 7:
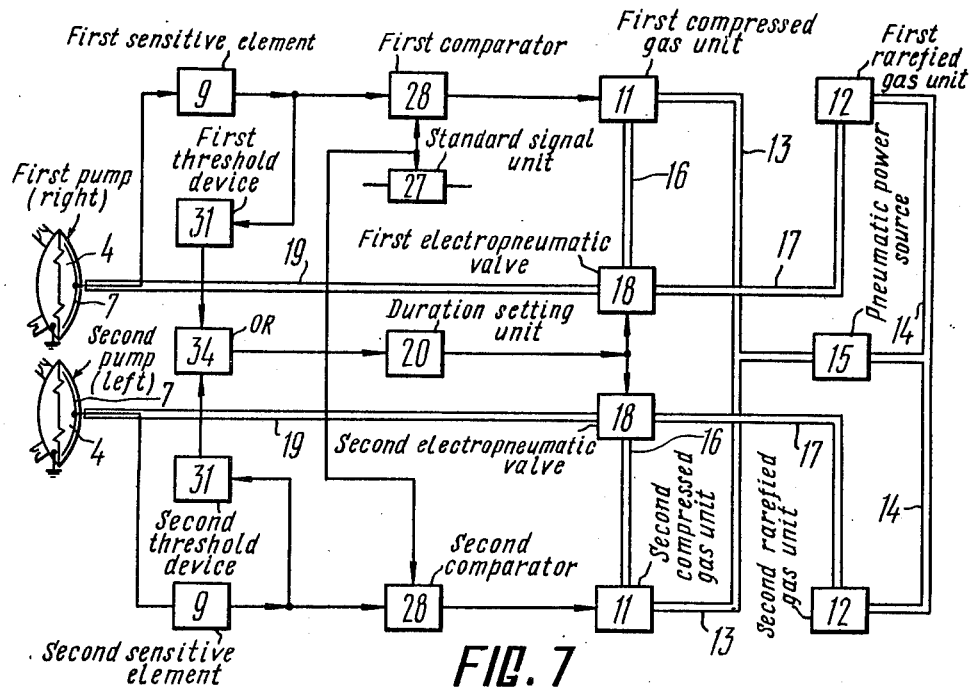
FIG. 7 is a block diagram of an artificial heart which equalizes the exchange of blood between the greater and lesser circulations by changing the compressed gas pressure, in accordance with the invention.

The control system shown in FIG. 7 is intended to equalize the exchange of blood between the greater and lesser circulations irrespective of changes in the peripheral vascular resistance and stabilizes the stroke volume of the pump which is the first to be filled.

In this control system, the control circuit of each pump includes the blood volume transducer 7 connected to the sensitive element 9 whose output is connected to one of the inputs of the comparator 28 and the input of the threshold device 31. The other input of the comparator 28 is connected to the electric input of the compressed gas unit 11 of the respective pump. The pneumatic input of the compressed gas unit 11 is connected to the pneumatic power source 15, to whose other output there is connected the input of the rarefied gas unit 12. The outlets of the units 11 and 12 are connected by the lines 16 and 17 to the respective pneumatic inputs of the electropneumatic valve 18. The output of the valve 18 is connected by the pneumatic line 19 to the pump's nipple 8.

The electric inputs of the electropneumatic valves 18 of both pumps are connected to the duration setting unit 20 which is common for both pumps. The input of the unit 20 is connected to the output of a logical OR element 34 having two inputs which are connected to the outputs of the threshold devices 31 of the respective pumps.

The function of the OR element 34 can be performed by any electronic device which can produce a pulse signal at its output in the presence of a signal across at least one of its two inputs.

In the case of the artificial heart of FIG. 7, an equal exchange of blood between the greater and smaller circulations irrespective of changes in the peripheral vascular resistance, and a stable stroke volume of the pump to be first filled with blood are provided for by changing the pressure of compressed gas and keeping constant the duration of its intake. The same object can be attained by automatically changing the duration of the compressed gas intake, while keeping at a constant level the pressure of compressed gas directed to the pneumatic chambers of the pumps. The result is a simplified pump control system.

Figure 8:
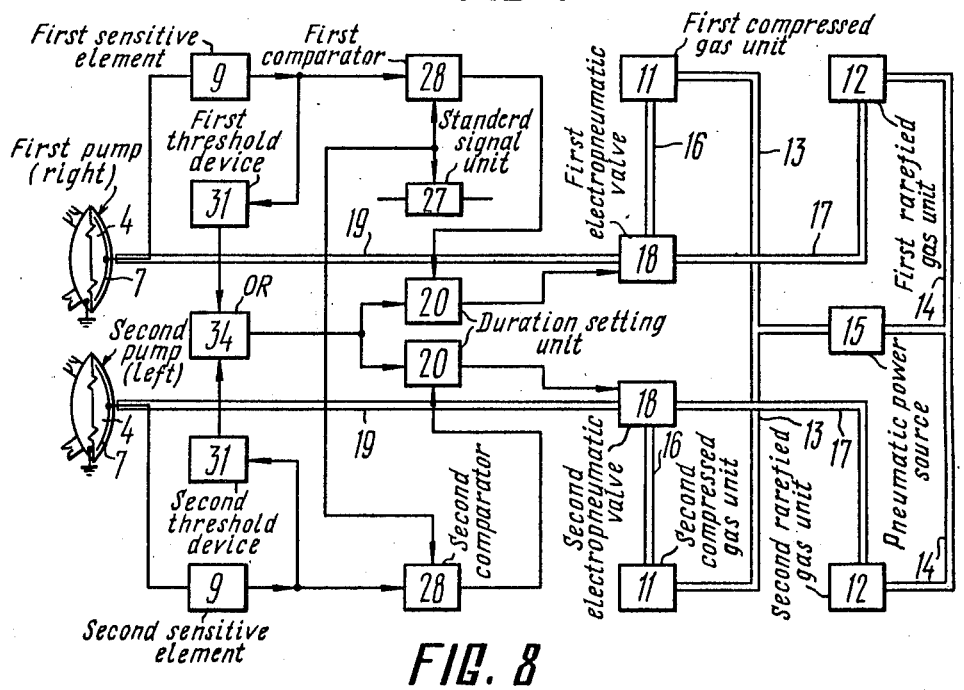
FIG. 8 is a block diagram of an artificial heart which equalizes the exchange of blood between the greater and lesser circulations by changing the duration of the compressed gas intake, in accordance with the invention.

A block diagram of such a device is shown in FIG. 8.

The system for controlling the supply and discharge of gas comprises two units 20 for setting the duration of the supply of gas, connected with their outputs to the electric inputs of the electropneumatic valves 18 of the respective pumps. Each of the units 20 has two inputs. With their first inputs, the units 20 are connected in parallel with the output of the logical OR element 34, whereas their second inputs are connected to the respective comparators 28.

The proposed artificial heart of the type that comprises one pump, a system for controlling the supply of gas to and the discharge of gas from the pneumatic chamber of said pump, and an indicator of the instantaneous volume of blood in the hydraulic chamber operates as follows.

Blood from the vein enters through the inlet valve 5 (FIG. 1) the hydraulic chamber 3 of the pump 1. The generator 21 actuates the duration setting unit 20. The latter's time setting unit shapes a square pulse corresponding to the systole phase of the pump.

As this signal is produced, the electropneumatic valve 18 connects, by means of the lines 19 and 16, the chamber 4 to the compressed gas unit 11. The compressed gas acts on the diaphragm 2 and forces the blood from the chamber 3 through the outlet valve 6 to the arterial bed. As this takes place, the diaphragm 2 is brought away from the stationary wall of the chamber 4, which changes the transducer's capacity. This change is sensed by the sensitive element 9 which converts it to a voltage amplitude at its output. Said voltage controls the current of the indicator 10 whose luminescence band is proportional to the control current and, consequently, the volume of blood forced from the chamber 3.

Upon the end of the square pulse, whose duration is set by the unit 20, voltage is removed from the electropneumatic valve 18, and the latter connects the chamber 4 through the lines 19 and 17 to the rarefied gas unit 12 (which may also be referred to as a vacuum unit). The rarefaction deflects the diaphragm 2, and the chamber 3 is filled with blood supplied through the inlet valve 5 until the arrival of the next clock pulse from the generator 21. The cycle is then repeated.

The presence of the transducer and indicator of the volume of blood in the hydraulic chamber of the pump considerably simplifies operation of the artificial heart and makes it possible to directionally change the parameters of the compressed gas unit and control system without using any blood pressure transducers or blood flow rate measuring instruments.

When the proposed artificial heart is employed in auxiliary circulation systems, it is sufficient to use an electrocardioscope, for example, of the double-channel type, with an adjustable delay of the output signal with respect to the R wave, whose output is connected to the input of the duration setting unit 20 instead of the clock pulse generator 21.

Connecting the output of the sensitive element 9 to the second input of the oscilloscope, one can control the duration of the pump's systole, taking into account all the delays of the control system and avoiding its coincidence in time with the systole of the natural heart, which makes it possible to effectively help the ailing heart under the counterpulsation conditions. Operation of the sensitive element 9 is illustrated by the diagram of FIG. 2.

The reference frequency generator 22 feeds sinusoidal voltage to the RC bridge via the transformer 23. As the chamber 3 is filled with blood, the bridge is balanced by the resistors R1 and R2, for example, to a point corresponding to a minimum luminescence of the indicator 10. While the chamber 3 of the pump 1 is filled with blood or empties, the bridge is unbalanced due to the change in the capacity of the blood volume transducer C1. An a.c. signal is produced at the output of the RC bridge, which is modulated by the frequency at which the chamber is filled with blood and emptied. The signal is amplified to a desired value and detected by the diode D1, whereupon the filter C5, R5 filters out its high frequency component. The signal is then applied to the input of the emitter follower 25 which, in turn, controls the luminescence band of the indicator 10. As pointed out above, the luminescence band is dependent on the discharge volume of the chamber 3 and varies at a pulse repetition frequency of the generator 21 (FIG. 1).

FIG. 3 shows an artificial heart sensitive to variations in the artificial pressure.

As noted above, the compressed gas unit 11 is a conventional electropneumatic converter; the compressed gas pressure at its outlet is determined by the control current.

An increase or decrease in the arterial pressure brings about a corresponding change in the stroke volume of blood discharged from the chamber 3, as well a corresponding change in the value of the signal at the output of the sensitive element. This takes place during the predetermined time of connection of the pneumatic chamber 4 through the electropneumatic valve 18 to the compressed gas unit 11. A difference of voltages compared by the comparator 28 correspondingly changes the voltage at the output of said comparator 28, which accordingly changes the current which controls the compressed gas unit 11, The latter, in turn, changes the compressed gas pressure, which makes it possible to overcome the changed arterial pressure without altering the stroke volume of the pump.

In order to provide for a constant, low-pulsation voltage, proportional to the stroke volume of the pump, at the output of the sensitive element 9, it is necessary to increase the time constant of the RC circuit (see FIG. 2) formed by the resistor R5 and the capacitor C5.

A change in the arterial pressure brings about a corresponding change in the voltage at the output of the comparator 28 (FIG. 4), which changes the period of time during which the pneumatic chamber 4 is connected via the electropneumatic valve 18 and the lines 16 and 19 to the compressed gas unit 11.

An increase in the arterial pressure, as well as a change in the resistances of the pneumatic lines 13, 16 and 19 for the supply of compressed gas results in an increase in the duration of a signal at the output of the unit 20, corresponding to the systole phase, and vice versa.

Operation of the duration setting unit 20 is illustrated by the diagram of FIG. 5. With no signal at the output of the generator 21, the transistor T1 is non-conducting, the transistor T2 is driven into conduction, and the transistor T3 is non-conducting. The electropneumatic valve 18 connects the pneumatic chamber 4 to the rarefied gas unit 12. The capacitor C7 is charged through the resistor R7 and the conducting transistor T2 almost to the level of the supply voltage of the multivibrator 15.

Upon the arrival of a negative clock pulse from the generator 21, the transistor T2 is rendered non-conducting, the transistor T1 snaps into conduction, and so does the transistor T3, whereby a signal is produced for switching the electropneumatic valve 18.

The transistor T2 remains conducting until the capacitor C7 is recharged through the conducting transistor T1 and the resistor R8 with the voltage which at this moment is present at the output of the comparator 28; this voltage is determined by the difference of potentials at the outputs of the standard signal transducer 27 and the sensitive element 9 (FIG. 4). The greater the difference, the less the voltage at the output of the comparator 28, the greater the recharging time of the capacitor C7, and the greater the period of time during which the chamber 4 is connected to the compressed gas unit 11.

The artificial heart of FIG. 3, wherein the dash lines indicate the circuit components and the connections between them, operates as follows.

The threshold device 31 provides a signal to actuate the duration setting unit 20 as soon as the hydraulic chamber 3 is filled with blood. Consequently, if the pump 1 is rapidly filled with blood, there is a decrease in the duration of the pump's diastole phase, and vice versa. Hence, a change in the pump's rate and delivery.

There is only a small change in the blood pressure at the outlet of the first (right) pump connected in the lesser circulation, so the stroke blood volume of this pump varies within a limited range. Thus the signal at the output of the sensitive element 9 (FIG. 6) of the right pump, which is proportional to the stroke volume, only changes within a narrow range (as pointed out above, this pump serves as a reference or standard pump). A change in the blood pressure at the outlet of the second (left) pump, due to some developments occurring in the greater circulation, wherein said left pump is connected, changes the signal at the output of the sensitive element 9 of this pump. The difference between the signals at the input of the comparator 33 causes a change in the control current of the compressed gas unit 11 of the left pump, which changes the compressed gas pressure at the outlet of said unit 11 and makes the stroke blood volume of the left pump equal to that of the right pump.

A deliberate change in the stroke volume of the right pump, for example, by changing the pressure of compressed gas supplied by the unit 11 of this pump, will automatically change the stroke volume of the left pump. Thus the delivery of the left pump becomes equal to that of the right pump, so there is no pumping of blood from one circulation to the other. If the blood pressure in the venous bed of one of the pumps is greater than that of the other pump, which is indicative of a greater venous return in the respective circulation, the respective pump will be more rapidly filled to the initial volume. The volume transducer 7 (FIG. 7) and the sensitive element 9 connected thereto send a signal to the threshold device 31, which signal corresponds to complete filling of the respective pump. The signal actuates the threshold device 31 and, through the OR circuit 34, the unit 20 for setting the duration of compressed gas intake. The latter, in turn, produces a signal to actuate the electropneumatic valve 18 which connects the pneumatic chambers 4 of the pumps to the compressed gas units 11, which is followed by a discharge of blood from the pumps to the arterial beds. Due to the fact that the circulation is looped with the pumps and the stroke volume of one pump is always less than that of the other (because the former pump is not fully filled with blood during a prescribed period of time), the blood pressure in the venous bed of the latter pump is gradually decreased, so that blood is pumped from one circulation to the other until the deliveries of the pumps become equal. The stroke volume of the pump that is the first to be filled completely is maintained at a stable level regardless of changes in the peripheral vascular resistance of the respective circulation, due to the fact that the compressed gas pressure at the outlet of the compressed gas unit 11 of the respective pump is changed accordingly. This pressure is changed depending on the difference between two signals compared by the comparator 28, i.e. voltage applied from the transducer 27 (the standard signal corresponding to the final systolic blood volume of the pumps) and voltage applied from the sensitive element 9, corresponding to the actual final systolic volume. As the chamber 4 of one of the pumps is fully filled with blood, the second pump may not be filled completely if the venous return of the respective circulation is insufficient. Thus a shorter time is required for the discharge of blood from the second pump, which is taken care of by the duration setting unit 20 (FIG. 8) of the respective pump and the comparator 28 which compares the standard signal arriving from the transducer 27 and the signal of the sensitive element 9, which corresponds to the actual stroke volume. The output signal of the comparator 28 changes the period of time during which the pneumatic chamber is connected to the compressed gas unit 11 so as to ensure evacuation of blood to the final systolic volume set by the transducer 27 without changing the predetermined compressed gas pressure. A lesser duration of the compressed gas supply is required to evacuate a lesser volume of blood, and vice versa.

Due to the fact that the circulation is looped with the pumps and the stroke volume of the pump with insufficient venous return is less, there takes place gradual pumping of blood from one circulation to the other so that the deliveries of both pumps become equal.

It is clear from the foregoing that the present invention is concerned with a novel pump control means based on a novel blood volume transducer. The proposed pump control system incorporates simple and cheap components, but provides for an adequate exchange of blood between the greater and lesser circulations in steady-state conditions and effectively equalizes deliveries of the artificial heart's pumps in transient conditions. The proposed artificial heart is sensitive to the venous return; the stabilization of stroke volumes makes it sensitive to changes in the blood pressure at the pump's outlets.

The possibility of visually checking the evacuation of air from the hydraulic chamber significantly simplifies the implantation of the pumps. In addition, the simple design of the device for converting the signal of the blood volume transducer accounts for its sufficient stability.

While particular embodiments of the present invention have been shown and described, various modifications thereof will be apparent to those skilled in the art and therefore it is not intended that the invention be limited to the disclosed embodiments or to the details thereof and departures may be made therefrom within the spirit and scope of the invention as defined in the claims.

What is claimed is:

1. An artificial heart comprising at least one blood circulating pump having:

a housing;

a diaphragm arranged in said housing and dividing said housing into two chambers, i.e. a hydraulic chamber and a pneumatic chamber;

said hydraulic chamber having an inlet valve and an outlet valve which are adapted to be connected in the circulation of a patient;

said pneumatic chamber having a nipple for the supply and discharge of gas and a conducting transparent coating applied onto the internal wall of said pneumatic chamber so that said coating and the surface of the blood circulating in said hydraulic chamber form a capacitor whose capacity varies depending on changes in the volume of the hydraulic chamber, said capacitor serving as a blood volume transducer of the pump;

a system for controlling the supply of gas to and the discharge of gas from said pneumatic chamber of said pump, comprising:

an electric power source;

a pneumatic power source;

an element sensitive to changes in the volume of blood in said hydraulic chamber of said pump, which sensitive element is an RC bridge one of whose arms incorporates said blood volume transducer of said pump;

an indicator of the volume of blood in said hydraulic chamber of said pump, connected to said sensitive element;

a compressed gas unit having a pneumatic input and an output, said pneumatic input being connected by means of a pneumatic line to said pneumatic power source;

a rarefied gas unit having a pneumatic input and a pneumatic output, said pneumatic input being connected by means of a pneumatic line to said pneumatic power source;

an electropneumatic valve having two pneumatic inputs, an electric input and a pneumatic output, said pneumatic output being connected by means of a pneumatic line to said nipple of said pneumatic chamber of said pump, one of said pneumatic inputs being connected through a pneumatic line to said compresses gas unit, while the second pneumatic input is connected through a pneumatic line to said rarefield gas unit;

a clock pulse generator which performs the function of a pulse rate setting unit;

a unit for setting the duration of the compressed gas intake, having an electric input and an electric output, said electric input being connected to said clock pulse generator, whereas said electric output is connected to the electric input of said electropneumatic valve.

2. An artificial heart as claimed in claim 1, wherein said system for controlling the supply of gas to and the discharge of gas from said pneumatic chamber of said pump comprises:

an electric power source;

a pneumatic power source;

an element sensitive to changes in the volume of blood in said hydraulic chamber of said pump, which sensitive element is an RC bridge one of whose arms incorporates said blood volume transducer;

a standard signal transducer with a voltage at its output corresponding to the final systolic blood volume of the pump;

a comparator having two inputs and an output, one of said inputs being connected to the output of said sensitive element, while the second input is connected to the standard signal transducer;

a compressed gas unit having a pneumatic input, an electric input and a pneumatic output, said pneumatic input being connected by means of a pneumatic line to said pneumatic power source, whereas said electric input is connected to the output of said comparator;

a rarefied gas unit having a pneumatic input and a pneumatic outut, said pneumatic input being connected by means of a pneumatic line to said pneumatic power source;
an electropneumatic valve having two pneumatic inputs, an electric input and a pneumatic output, said pneumatic output being connected by means of a pneumatic line to said nipple of the pneumatic chamber of said pump, one of said pneumatic inputs being connected by means of a pneumatic line to said compressed gas unit, while the second pneumatic input is connected by means of a pneumatic line to said rarefied gas unit;
a clock pulse generator which performs the function of a pulse rate setting unit;
a unit for setting the duration of the compressed gas intake, having an electric input and an electric output, said electric input being connected to said clock pulse generator, whereas said electric output is connected to said electric input of said electropneumatic valve.

3. An artificial heart as claimed in claim 1, wherein said system for controlling the supply of gas to and the discharge of gas from said pneumatic chamber of said pump comprises:
an electric power source;
a pneumatic power source;
an element sensitive to changes in the volume of blood in said hydraulic chamber of said pump, which sensitive element is an RC bridge one of whose arms incorporates said blood volume trasducer of the pump;
a standard signal transducer with a voltage at its output corresponding to the final systolic blood volume of the pump;
a comparator having two inputs and an output, one of said inputs being connected to the output of said sensitive element, while the second input is connected to said standard signal transducer;
a compressed gas unit having a pneumatic input, a pneumatic output and an electric input, said pneumatic input being connected by means of a pneumatic line to said pneumatic power source, whereas the electric input is connected to the output of said comparator;
a rarefied gas unit having a pneumatic input and a pneumatic output, said pneumatic input being connected by means of a pneumatic line to said pneumatic power source;
an electropneumatic valve having two pneumatic inputs, an electric input and a pneumatic output, said pneumatic output being connected by means of a pneumatic line to said nipple of said pneumatic chamber of said pump, one of said pneumatic inputs being connected by means of a pneumatic line to said compressed gas unit, the second pneumatic input being connected by means of a pneumatic line to said rarefied gas unit;
a threshold device intended to register the initial volume, having an input and an output, said input being connected to the output of said sensitive element;
a unit for setting the duration of the compressed gas intake, having an electric input and output, said input being connected to said threshold device, whereas said output is connected to the electric input of said electropneumatic valve.

4. An artificial heart as claimed in claim 1, wherein said system for controlling the supply of gas to and the discharge of gas from said pneumatic chamber of said pump comprises:
an electric power source;
a pneumatic power source;
an element sensitive to changes in the volume of blood in said hydraulic chamber of said pump, which sensitive element is an RC bridge one of whose arms incorporates said blood volume transducer of said pump;
a standard signal transducer with a voltage at its output corresponding to the final systolic blood volume of the pump;
a comparator having two inputs and an output, one of said inputs being connected to the output of said sensitive element, the second input being connected to the standard signal transducer;
a compressed gas unit having a pneumatic input and a pneumatic output, said pneumatic input being connected by means of a pneumatic line to said pneumatic power source;
a rarefied gas unit having a pneumatic input and a pneumatic output, said pneumatic input being connected by means of a pneumatic line to said pneumatic power source;
an electropneumatic valve having two pneumatic inputs, an electric input and a pneumatic output, said pneumatic output being connected by means of a pneumatic line to said nipple of said pneumatic chamber of said pump, one of said pneumatic inputs being connected by means of a pneumatic line to said compressed gas unit, whereas the second pneumatic input is connected by means of a pneumatic line to said rarefied gas unit;
a clock pulse generator serving as a pulse rate setting unit;
a unit for setting the duration of the compressed gas intake, having two inputs and an output, one of said inputs being connected to said clock pulse generator, the second input being connected to the output of said comparator, whereas said output is connected to the electric input of said electropneumatic valve.

5. An artificial heart as claimed in claim 1, wherein said system for controlling the supply of gas to and the discharge of gas from said pneumatic chamber of said pump comprises:
an electric power source;
a pneumatic power source;
an element sensitive to changes in the volume of blood in said hydraulic chamber of said pump, which sensitive element in an RC bridge one of whose arms incorporates said blood volume trasducer of said pump;
a standard signal transducer with a voltage at its output corresponding to the final systolic blood volume of said pump;
a comparator having two inputs and an output, one of said inputs being connected to the output of said sensitive element, whereas the second input is connected to the standard signal transducer;
a compressed gas unit having a pneumatic input and a pneumatic output, said pneumatic input being connected by means of a pneumatic line to said pneumatic power source;
a rarefied gas unit having a pneumatic input and a pneumatic output, said pneumatic input being connected by means of a pneumatic line to said pneumatic power source;

an electropneumatic valve having two pneumatic inputs, an electric input and a pneumatic output, said pneumatic output being connected by means of a pneumatic line to said nipple of said pneumatic chamber of said pump, one of said pneumatic inputs being connected by means of a pneumatic line to said compressed gas unit, whereas the second pneumatic input is connected by means of a pneumatic line to said rarefied gas unit;

a threshold device having an input and an output, said input being connected to the output of said sensitive element;

a unit for setting the duration of the compressed gas intake, having two inputs and an output, one of said inputs being connected to the output of said threshold device, the second input being connected to the output of said comparator, whereas the output is connected to the electric input of said electropneumatic valve.

6. An artificial heart as claimed in claim 1, having two blood circulating pumps referred to as a first pump and a second pump, each of said pumps comprising:

a housing;

a diaphragm arranged in said housing and dividing it into two chambers which are:

a hydraulic chamber having inlet and outlet valves, the inlet and outlet valves of one of said pumps being adapted to be connected in the lesser circulation, whereas the inlet and outlet valves of the other of said pumps are adapted to be connected in the greater circulation;

a pneumatic chamber having a nipple for the supply and discharge of gas and a conductive coating applied onto the internal wall of said pneumatic chamber, said coating and the surface of the blood circulating in said hydraulic chamber forming a capacitor whose capacity varies depending on changes in the volume of blood in said hydraulic chamber, said capacitor serving as the blood volume transducer of the pump;

said artificial heart further including a system for controlling the supply of gas to and the discharge of gas from said pneumatic chambers of said pumps, which control system comprises:

an electric power source;

a pneumatic power source;

a first element sensitive to changes in the volume of blood in the respective hydraulic chamber of the first of said pumps, which sensitive element is an RC bridge one of whose arms incorporates said blood volume transducer of said first pump;

a second element sensitive to changes in the volume of blood in the respective hydraulic chamber of the second of said pumps, which sensitive element is an RC bridge one of whose arms incorporates said blood volume transducer of said second pump;

a first indicator to indicate the volume of blood in said hydraulic chamber of said first pump, connected to said first sensitive element;

a second indicator to indicate the volume of blood in said hydraulic chamber of said second pump, connected to said second sensitive element;

two compressed gas units, one for each pump, each of said units having a pneumatic input and a pneumatic output, said input being connected by means of a pneumatic line to said pneumatic power source;

two rarefied gas units, one for each pump, each of said units having a pneumatic input and a pneumatic output, said input being connected by means of a pneumatic line to said pneumatic power source;

a first electropneumatic valve having two pneumatic inputs, an electric input and a pneumatic output, said pneumatic output being connected by means of a pneumatic line to said nipple of said pneumatic chamber of said first pump, one of said pneumatic inputs being connected by means of a pneumatic line to said compressed gas unit, the second pneumatic input being connected by means of a pneumatic line to said rarefied gas unit;

a second electropneumatic valve having two pneumatic inputs, an electric input and a pneumatic output, said pneumatic output being connected by means of a pneumatic line to said nipple of said pneumatic chamber of said second pump, one of said pneumatic inputs being connected by means of a pneumatic line to the second compressed gas unit, the second pneumatic input being connected by means of a pneumatic line to the second rarefied gas unit;

a clock pulse generator serving as the pulse rate setting unit;

a unit for setting the duration of the compressed gas intake, having an input and an output, said input being connected to said clock pulse generator, whereas said output is connected to the electric inputs of both said electropneumatic valves.

7. An artificial heart as claimed in claim 6, wherein said system for controlling the supply of gas to and the discharge of gas from said pneumatic chambers of said first and second pumps comprises:

an electric power source;

a pneumatic power source;

a first element sensitive to changes in the volume of blood in said hydraulic chamber of said first pump, which sensitive element is an RC bridge one of whose arms incorpprates said blood volume transducer of said first pump;

a second element sensitive to changes in the volume of blood in said hydraulic chamber of said second pump, which sensitive element is an RC bridge one of whose arms inroporates said blood volume transducer of said second pump;

a comparator having two inputs and an output, one of said inputs being connected to the output of said first sensitive element, the second of said inputs being connected to the output of said second sensitive element;

a first compresses gas unit having a pneumatic input and a pneumatic output, said pneumatic input being connected by means of a pneumatic line to said pneumatic power source;

a second compressed gas unit having a pneumatic input, a pneumatic output and an electric input, said pneumatic input being connected by means of a pneumatic line to said pneumatic power source, whereas the electric input is connected to the output of said comparator;

two rarefied gas units, one for each pump, each of said rarefied gas units having a pneumatic input and a pneumatic output, said pneumatic input being connected by means of a pneumatic line to said pneumatic power source;

a first electropneumatic valve having two pneumatic inputs, an electric input and a pneumatic output, said pneumatic output being connected by means of a pneumatic line to said nipple of said pneumatic chamber of said first pump, one of said pneumatic inputs being connected by means of a pneumatic line to one of said compressed gas units, the second pneumatic input being connected by means of a pneumatic line to one of said rarefied gas units;

a second electropneumatic valve having two pneumatic inputs, an electric input and a pneumatic output, said pneumatic output being connected by means of a pneumatic line to said nipple of said pneumatic chamber of said second pump, one of said pneumatic inputs being connected by means of a pneumatic line to said second compressed gas unit, the second pneumatic input being connected by means of a pneumatic line to said second rarefied gas unit;

a clock pulse generator serving as a pulse rate setting unit;

a unit for setting the duration of the compressed gas intake, having an input and an output, said input being connected to said clock pulse generator, whereas said output is connected to said electric inputs of both said electropneumatic valves.

8. An artificial heart as claimed in claim 6, wherein said system for controlling the supply of gas to and the discharge of gas from said pneumatic chambers of said two pumps comprises:

an electric power source;
a pneumatic power source;
a first element sensitive to changes in the volume of blood in said hydraulic chamber of said first pump, which sensitive element is an RC bridge one of whose arms incorporates said blood volume transducer of said first pump;

a second element sensitive to changes in the volume of blood in said hydraulic chamber of said second pump, which sensitive element is an RC bridge one of whose arms incorporates said blood volume transducer of said second pump;

a standard signal transducer with a voltage at its output corresponding to the final systolic blood volume of the pump;

a first comparator having two inputs and an output, one of said inputs being connected to the output of said first sensitive element of said first pump, the second input being connected to the output of said standard signal transducer;

a second comparator having two inputs and an output, one of said inputs being connected to the output of said second sensitive element of said second pump, the second input being connected to the output of said standard signal transducer;

a first compressed gas unit having a pneumatic input, an electric input and a pneumatic output, said pneumatic input being connected by means of a pneumatic line to said pneumatic power source, said electric input being connected to the output of said first comparator;

a second compressed gas unit having a pneumatic input, an electric input and a pneumatic output, said pneumatic input being connected by means of a pneumatic line to said pneumatic power source, the electric input being connected to the output of said second comparator;

two rarefied gas units, one for each pump, each of said rarefied gas units having a pneumatic input and a pneumatic output, said pneumatic input being connected by means of a pneumatic line to said pneumatic power source;

a first electropneumatic valve having two pneumatic inputs, an electric input and a pneumatic output, said pneumatic output being connected by means of a pneumatic line to said nipple of said pneumatic chamber of said first pump, one of said pneumatic inputs being connected by means of a pneumatic line to said first compressed gas unit, the second pneumatic input being connected by means of a pneumatic line to said first rarefied gas unit;

a second electropneumatic valve having two pneumatic inputs, an electric input and a pneumatic output, said pneumatic output being connected by means of a pneumatic line to said nipple of said pneumatic chamber of said second pump, one of said pneumatic inputs being connected by means of a pneumatic line to said second compressed gas unit, the second pneumatic input being connected by means of a pneumatic line to said second rarefied gas unit;

a first threshold device intended to register the initial volume of blood in said hydraulic chamber of said first pump, whose input is connected to the output of said first sensitive element;

a second threshold device intended to register the initial volume of blood in said hydraulic chamber of said second pump, whose input is connected to the output of said second sensitive element;

a logical OR element having two inputs and an output, one of said inputs being connected to the output of said first threshold device, the second input being connected to the output of said second threshold device;

a unit for setting the duration of the compressed gas intake, having an electric input and an electric output, said input being connected to the output of said logical OR element, the output of said duration setting unit being connected to the electric inputs of said electropneumatic valves.

9. An artificial heart as claimed in claim 6, wherein said system for controlling the supply of gas to and the discharge of gas from said pneumatic chambers of said two pumps comprises:

an electric power source;
a pneumatic power source;
a first element sensitive to changes in the volume of blood in said hydraulic chamber of said first pump, which sensitive element is an RC bridge one of whose arms incorporates said blood volume transducer of said first pump;

a second element sensitive to changes in the volume of blood in said hydraulic chamber of said second pump, which sensitive element is an RC bridge one of whose arms incorporates said blood volume transducer of said second pump;

a standard signal transducer with a voltage at its output corresponding to the final systolic blood volume;

a first comparator having two inputs and an output, one of said inputs being connected to the output of said first sensitive element, the second input being connected to the output of said standard signal transducer;

a second comparator having two inputs and an output, one of said inputs being connected to the output of said second sensitive element, the second input being connected to the output of said standard signal transducer;

two compressed gas units, one for each pump, each of said compressed gas units having a pneumatic input and a pneumatic output, said pneumatic input being connected by means of a pneumatic line to said pneumatic power source;

two rarefied gas units, one for each pump, each of said rarefied gas units having a pneumatic input and a pneumatic output, said pneumatic input being connected by means of a pneumatic line to said pneumatic power source;

a first electropneumatic valve having two pneumatic inputs, an electric input and a pneumatic output, said pneumatic output being connected by means of a pneumatic line to said nipple of said pneumatic chamber of said first pump, one of said pneumatic inputs being connected by means of a pneumatic line to said first compressed gas unit, the second pneumatic input being connected by means of a pneumatic line to said first rarefied gas unit;

a second eletropneumatic valve having two pneumatic inputs, an electric input and a pneumatic output, said pneumatic output being connected by means of a pneumatic line to said nipple of said pneumatic chamber of said second pump, one of said pneumatic inputs being connected by means of a pneumatic line to said second compressed gas unit, the second pneumatic input being connected by means of a pneumatic line to said second rarefied gas unit;

a first threshold device intended to register the initial volume of blood in said hydraulic chamber of said first pump, its input being connected to the output of said first sensitive element;

a second threshold device intended to register the initial volume of blood in said hydraulic chamber of said second pump, its input being connected to the output of said second sensitive element;

a logical OR element having two inputs and an output, one of said inputs being connected to the output of said first threshold device, the second input being connected to the output of said second threshold device;

a first unit for setting the duration of the compressed gas intake, having two inputs and an output, one of said inputs being connected to the output of said logical OR element, the second input being connected to the output of said first comparator, the output being connected to the electric input of said first electropneumatic valve;

a second unit for setting the duration of the compressed gas intake, having two inputs and an output, one of said inputs being connected to the output of said logical OR element, the second input being connected to the output of said second comparator, the output being connected to the electric input of said second electropneumatic valve.

* * * * *